United States Patent [19]

Bodanszky

[11] 3,944,538

[45] Mar. 16, 1976

[54] PROCESS AND APPARATUS FOR THE SYNTHESIS OF PEPTIDES NOT LINKED TO POLYMERS

[76] Inventor: Miklos Bodanszky, 18035 Fernway Road, Shaker Heights, Ohio 44122

[22] Filed: Oct. 2, 1973

[21] Appl. No.: 402,765

[52] U.S. Cl............................ 260/112.5 R; 23/286
[51] Int. Cl.²................... C07C 103/52; C07G 7/00
[58] Field of Search................................. 260/112.5

[56] References Cited
UNITED STATES PATENTS

| 3,531,258 | 9/1970 | Merrifield et al................ 260/112.5 |
| 3,557,077 | 1/1971 | Brunfeldt et al................. 260/112.5 |
| 3,647,390 | 3/1972 | Kubodera et al................ 260/112.5 |
| 3,715,190 | 2/1973 | Park et al........................ 260/112.5 |
| 3,846,398 | 11/1974 | Hirschmann et al............ 260/112.5 |
| 3,846,399 | 11/1974 | Hirschmann et al............ 260/112.5 |

*Primary Examiner*—Lewis Gotts
*Assistant Examiner*—Reginald J. Suyat
*Attorney, Agent, or Firm*—Lowe, King, Price & Markva

[57] ABSTRACT

In situ process for synthesizing peptides not linked to polymers. The peptide derivatives remain in the same reaction vessel throughout the chain-lengthening procedure. Preferred apparatus for performing the process comprises means for mixing, evaporation and centrifugation.

20 Claims, 1 Drawing Figure

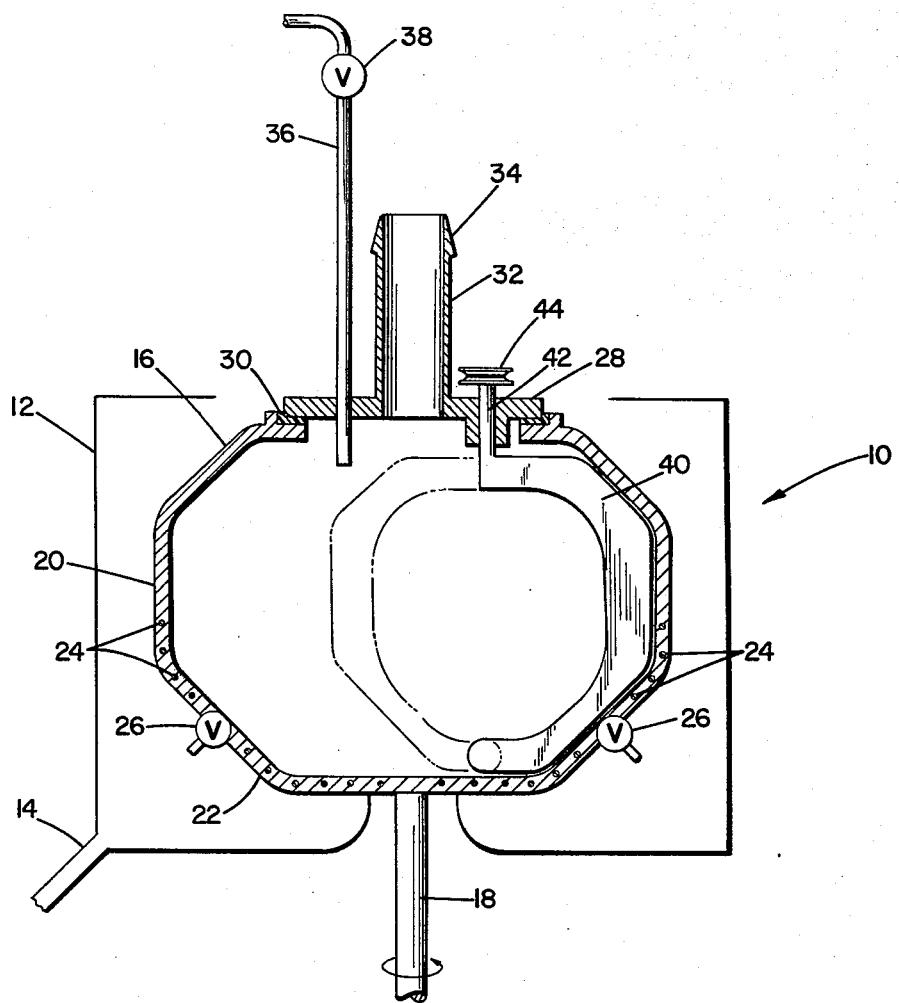

PROCESS AND APPARATUS FOR THE SYNTHESIS OF PEPTIDES NOT LINKED TO POLYMERS

BACKGROUND OF THE INVENTION

1. Field of the Invention

This invention aims at the efficient synthesis of peptide chains. It involves a procedure and an apparatus that allows the execution of this procedure with convenience and expediency.

2. Prior Art

The numerous and cumbersome operations which are necessary during the multi-step synthesis of a peptide chain led to the development of solid-phase techniques (cfr. R. B. Merrifield, J. Amer. Chem. Soc., 85, 2149 (1963) and R. L. Letsinger and M. J. Kornet, J. Amer. Chem. Soc. 85, 3045 (1963)) and to schemes that are based on soluble polymers (cfr. M. M. Shemyakin, Y. A. Ovchinnikov and A. A. Kiryushkin, Tetrahedron Lett. 1965, 2323). In these techniques, an amino acid (or peptide) is chemically attached to a polymeric support and acylation, the removal of blocking group, second acylation, etc., are carried out on the polymer-amino acid or polymer-peptide combination. The small molecular weight reactants and byproducts are easily separated from the large molecular weight product and therefore a facilitation of the operations and the automation of these operations becomes possible. On the other hand, the use of polymeric supports necessitates two steps that are often not simple enough: (a) the formation of a bond between the first constituent and the polymer, and (b) the cleavage of the bond between the completed peptide chain and the polymer. Furthermore, the synthetic procedures based on polymeric support suffer from several other disadvantages as well, such as decreased availability of analytical controls or the difficulty of purifying intermediates if this becomes necessary.

SUMMARY OF THE INVENTION

The present invention aims at a convenient and efficient route to synthetic peptides through isolated, pure intermediates that — if necessary — can be further purified at any selected stage. The process of the invention is an in situ synthesis process comprising cycles each involving removal of an amino-protecting group from a protected peptide not bound to a polymer, and acylation with an N-protected amino acid in activated form, the characterizing feature of said process being that the peptide derivatives remain in the same reaction vessel throughout the chain-lengthening procedure.

DETAILED DESCRIPTION OF THE INVENTION

The process of the invention is based on the observation (cfr. M. Bodanszky, Ann. New York. Acad. Sci. 88, 655 (1960)) that, especially with selective acylating agents, protected peptides can be obtained which in turn can be separated from excess acylating agent and byproducts by an appropriately chosen combination of solvents, and thereby secured in essentially pure form, generally ready for the next chain lengthening steps.

An example of an embodiment of the process of the invention is the following:

A peptide protected at its N-terminal with t-butyloxycarbonyl group is briefly treated with trifluoroacetic acid, this acid removed in vacuo, the residue treated with ether and the trifluoroacetate salt is isolated by filtration or centrifugation. To a solution of this salt in dimethylformamide, an equivalent amount of tertiary base, e.g., triethylamine or diisopropylethylamine, is added followed by the amino acid to be incorporated, in protected and activated form, such as t-butyloxycarbonyl amino acid o-nitrophenyl ester. To provide practical reaction rates and complete acylation of the amino component, the acylating agent is applied in excess. The completion of the reaction is monitored by color reactions (e.g., disappearance of the ninhydrin color) or by measuring the amount of the leaving group (e.g. nitrophenol) liberated. This can be done by determining the light absorption of the solution at a suitable wavelength. When the completeness of the acylation reaction is ascertained, the solvent is removed in vacuo and the residue is treated with a "nonsolvent" such as ethyl acetate, that precipitates the product, the desired protected peptide, but keeps the excess active ester and the byproducts (nitrophenol, diisopropylethylamine trifluoroacetate or triethylamine trifluoroacetate) in solution. The solid product is separated from the solution by centrifugation or filtration and washed with ethyl acetate. The remaining portion of this "nonsolvent" is removed by evaporation in vacuo or with the help of a stream of nitrogen. The dry, solid product is a protected peptide corresponding to the starting material but lengthened by one amino acid residue, and it is now ready for the next cycle: deblocking with trifluoroacetic acid, etc.

It is a characteristic feature of this procedure that the peptide derivatives remain in the same reaction vessel throughout the chain-lengthening procedure.

In its broad aspect, the present invention relates to a process for synthesizing peptides, comprising deblocking an N-protected non-polymer bound peptide derivative and acylating the liberated peptide derivative with an N-protected amino acid in activated form, with the characterizing feature that the peptide is kept in the same vessel throughout the chain-lengthening procedure.

The term "non-polymer-bound peptide" as used in the present specification and claims is intended to indicate a peptide which, contradistinction to the peptides and peptide derivatives chain-lengthened according to the techniques of Merrifield (loc.cit.) and Shemyakin et al. (loc.cit.), is not bound to an insoluble or soluble non-peptide polymer.

A peptide synthesis usually involves several cycles of chain-lengthening by deblocking and acylation, and when carried out according to the principles of the present invention, such synthesis can be defined as a synthesis comprising cycles, each of which comprises deblocking an N-protected non-polymer-bound peptide derivative and acylating the liberated peptide derivative with an N-protected amino acid in activated form (or in some of the cycles, the acylating reactant may be an N-protected peptide in activated form), with the characterizing feature that the peptide intermediates are kept in the same vessel throughout said cycles. However, if desired, the peptide intermediate may be removed for special purification treatments at any stage, and then returned to the vessel for further treatment.

More detailed, a preferred embodiment of the invention relates to a process comprising addition of acid to a protected peptide contained in a vessel to acidolytically remove an amino-protecting group from the peptide, precipitation of the resulting salt of the liberated peptide in the vessel by addition of a precipitant thereof, separation of the liquid phase from the precipitate while retaining the precipitate in the vessel, washing of the precipitate in the vessel, dissolution of the precipitate in the vessel by addition of a solvent thereof, addition of a base, acylation of the dissolved peptide in the vessel with an N-protected amino acid in activated form, precipitation of the resulting protected chain-lengthened peptide derivative by addition of a nonsolvent thereof to the vessel, separation of the liquid phase from the precipitate while retaining the precipitate in the vessel, and washing of the precipitate in the vessel.

In the first cycle of a process involving a series of cycles comprising these operations, the derivative to be acylated may be an amino acid instead of a peptide, but too great solubility of shorter chain intermediates in common organic solvents that can keep the byproducts etc. in solution will often dictate the use of a peptide of a certain chain length as starting material.

The acidolytical removal of an amino-protecting group, e.g. a t-butyloxycarbonyl group or a benzyloxycarbonyl group, may be performed using an acid suitable for this purpose, e.g. trifluoroacetic acid, HBr in acetic acid, or HCl in acetic acid. The acid is added in excess to the protected peptide contained in a suitable reaction vessel, and dissolution occurs. After the desired reaction time, the acid may preferably be removed, suitably by evaporation in vacuo from the vessel. The residue is thereafter treated with a precipitant such as dialkyl ether, e.g. dipropyl ether, diisopropyl ether or, preferably, diethyl ether, which is then separated from the precipitated salt by filtration or centrifugation in such a manner that the precipitate remains in the vessel. It is preferred to perform a washing operation by addition of another portion of the precipitant and renewed separation thereof from the precipitate.

After the final separation of the precipitant, it may be preferred to dry the precipitate, e.g. in vacuo, established by connecting the vessel interior to a suitable vacuum source, and/or in a stream of inert gas introduced into the vessel. Thereafter, the salt of the liberated peptide in the vessel is dissolved by adding a solvent suitable for the acylation, e.g. dimethylformamide or dimethylsulfoxide, whereupon a base, suitably a tertiary amine or a quaternary ammonium hydroxide, is added. As examples of preferred bases may be mentioned triethylamine, diisopropylethylamine, and N-methylmorpholine. Simultaneously with or subsequently to the addition of the base, the amino acid to be incorporated is added. While the incorporation of peptides rather than amino acids is also possible and the coupling reaction can be carried out by means of coupling reagents as well (cfr. Y. S. Klausner and M. Bodanszky, Synthesis 1972, 453), the preferred execution of the procedure is entirely stepwise (cfr. M. Bodanszky, Ann. New York, Acad. Sci. 88, 655 (1960)) with single amino acid residues in their protected and activated form used for chain-lengthening. Optimal results were obtained with amino acids protected on their α-amino group with urethane-type protecting groups such as benzyloxycarbonyl or tert.butyloxycarbonyl and activated in the form of p-nitrophenyl esters, o-nitrophenyl esters, etc. Also symmetrical anhydrides deserve to be mentioned as activated derivatives. Functions

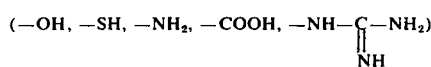

in the side chains of the amino acid residues are protected by conventionally used protecting groups (cfr. M. Bodanszky and M. A. Ondetti, Peptide Synthesis, Wiley Interscience Publishers, New York, 1966, pages 54 – 63). The activation of the protected amino acids can be carried out in the reaction vessel, but it is preferred to prepare these reactive intermediates separately and to add them in activated, and, if possible purified form to the reaction mixture that contains the amino component to be acylated. As indicated above, the acylating agent is suitably applied in excess, and the acylating agent is preferably added under thorough mixing or agitation. Some peptides are, due to the character of their side-chain functions, difficult to solve in inert solvents usable for the acylation stage, and it may therefore be necessary or desirable to acylate them not in dissolved form, but rather in suspension in a suitable solvent. The term "dissolution" as used above and in the claims is intended to cover also the case where no clear solution, but rather a suspension, results.

When the acylation reaction is completed (which may be ascertained as indicated above), the resulting protected chain-lengthened peptide derivative is precipitated by addition of a nonsolvent thereof to the vessel. However, in most cases it is preferred to remove the major part of the solvent before the nonsolvent is added. The removal of the solvent is suitably performed by evaporation in vacuo from the vessel. The choice of nonsolvent to be used in the precipitation of the chain-lengthened peptide derivative will depend on various factors. Usually, the nonsolvent will be an organic liquid, but also for example water may in some circumstances come into consideration. At any rate, in each case a nonsolvent should be chosen which will precipitate the product, the desired protected peptide, but keep the excess of acylating agent and the by-products present in solution. Thus, when trifluoroacetic acid has been used in the deblocking step, ethyl acetate will often be a suitable nonsolvent. When HCl in acetic acid has been used for deblocking, chloroform may be the preferred nonsolvent, and another nonsolvent which has been found useful in combination with HBr in acetic acid as deblocking agent and dimethylformamide as solvent for acylation in the presence of a tertiary base is 95% ethanol.

After the precipitation of the desired chain-lengthened peptide derivative with the nonsolvent, the liquid phase comprising the nonsolvent and the components dissolved therein is separated from the precipitate by filtration or centrifugation in such a manner that the precipitate remains in the vessel, and preferably, a further portion of nonsolvent is then added to wash the precipitate in the vessel and subsequently separate it from the washed precipitate. It is often preferred to subsequently remove the remaining portion of the nonsolvent, e.g. by evaporation in vacuo and/or by means of a stream of an inert gas such as nitrogen.

While the process of the invention may be carried out in existing apparatus components, possibly with small modification (and, in the below example of execution, is indeed, carried out in only slightly modified existing apparatus designed for other purposes), one aspect of the invention relates to an especially suitable apparatus which makes possible the execution of the process of the invention in an especially advantageous way.

In its broadest aspect, the apparatus of the invention is an apparatus for performing peptide syntheses, comprising a reaction vessel and means for rotating said vessel so as to separate liquid and solid phases in said vessel by centrifugal forces. Preferably, means for removing separated liquid phase from said vessel constitute integrated parts of the apparatus, and also means for promoting evaporation of liquid, including means for heating the contents of the vessel, are preferably incorporated in the apparatus. The evaporation promoting means may suitably comprise means for establishing subatmospheric pressure in the vessel, including a conduit connectable to a vacuum source. To obtain proper mixing or agitation during the acylation stage, the apparatus preferably comprises agitating means.

One aspect of the apparatus of the invention is a centrifuge provided with a mixing device that also permits the evaporation of solvents (and of the nonsolvent) in vacuo and/or by a stream of nitrogen or other inert gas. A useful form of this apparatus consists of a vertical, cylindrical vessel that can be rotated around its vertical axis. At high rotation rates, it performs the functions of a sedimentation centrifuge; at lower rates, with a scraper-mixer lowered into it, it is a mixing vessel. The vessel is equipped with tubes for the addition of reactants and with valves or tubes that will syphon off solutions of the byproducts and excess reagents in the nonsolvent, and also with a removable vacuum-tight cover with conduit which will allow the removal of solvents by distillation in vacuo. During distillation, heat is applied, e.g. by means of a heating mantle, to provide for the latent-heat of evaporation. The cylindrical vessel is constructed from acid-resistant material or is lined with such a material (e.g. silver, teflon, polypropylene, etc.). This apparatus permits deblocking with e.g. trifluoroacetic acid, removal of this acid, precipitation with e.g. ether, separation of the trifluoroacetate salts from the ether solutions, drying of these salts, their dissolution in e.g. dimethylformamide, the addition of a tertiary base and of a protected amino acid in activated form, the monitoring of the acylation reaction by withdrawing of small probes, the evaporation of the solvent (dimethylformamide), the addition of a nonsolvent (e.g. ethyl acetate), separation of the insoluble product, the lengthened peptide chain, from the excess acylating agent and byproducts, the washing of the product with the nonsolvent and the drying of the product. While a filter centrifuge or other devices for separation of solid and liquid can also be applied, the preferred instrument is based on sedimentation by centrifugation.

Since the protected derivatives of peptides with gradually increasing chain length remain in the same vessel throughout the chain-lengthening procedure, mechanical losses are greatly diminished and the process can be automated with the aid of well-known programming devices.

DESCRIPTION OF THE DRAWING

The drawing shows an embodiment of an apparatus 10 for performing in situ peptides syntheses. In a housing 12 with a drainage conduit 14, a centrifuge vessel 16 having a shaft 18 is rotatably mounted. The centrifuge vessel 16 comprises a cylindrical wall section 20 and a lower converging wall section 22. In the side walls and the bottom of the centrifuge vessel, electrical heating coils 24 are arranged to serve as means for heating the contents of the vessel during e.g. evaporation and drying operations. Alternatively, a heating mantle (not shown) could be arranged around the vessel. In the lower part 22 of the centrifuge vessel, valves 26 are mounted through which supernatant liquid can be removed during centrifugation when the precipitate has collected along the vertical-cylindrical wall 20. The valves may e.g. be operated electrically, or they may be designed so as to open at a predetermined centrifugal force, possibly with some delay. A cover 28 may be mounted vacuum-tightly on the centrifuge vessel 16, using sealing means 30. The cover 28 is equipped with a tube 32 having a connecting means 34, e.g. in the form of a standard tapered joint as shown, for connection to a vacuum-source (not shown) through suitable valve means (not shown). A conduit 36 with a valve 38 is mounted in the cover 28 and may be used for addition of liquid reactants, and also for the addition of an inert gas serving as drying medium. Furthermore, when the conduit 36 is lowered into the centrifuge vessel 16, it may be used for suction of liquid from the centrifuge vessel, for example when a precipitate has sedimented on the vertical wall 20 of the vessel, and the supernatant liquid has collected in the bottom part of the centrifuge vessel (in other words, when the valves 26 have not been used for withdrawal of liquid during centrifugation, or when not all of the supernatant liquid had been removed through the valves during the centrifugation). A scraper-stirrer 40 mounted in the cover 28 is rotatable around the axis of its shaft carrying a pulley 44, by means of which the stirrer 40 can be rotated by means of e.g. a motor (not shown). When the cover 28 is mounted on the centrifuge vessel or removed therefrom, the stirrer 40 may be positioned as indicated by the dotted lines so that it does not interfere with the mounting-dismounting operations.

The apparatus 10 permits separation of liquid from precipitate be centrifugation at high rotational speeds around the axis of the shaft 18. During high speed rotation, the cover 28 may be lifted so that it no longer contacts the centrifuge vessel 16, or the seal 30 may be of a type which permits high speed rotation of the centrifuge vessel 16 while the cover 28 remains non-rotating. Furthermore, during high speed rotation of the centrifuge vessel 16, the scraper-stirrer 40 may be positioned as indicated by the dotted lines so that it will not give rise to any problematic turbulence in the centrifuge contents. Supernatant liquid may be removed during the centrifugation operation by means of the valves 26, and/or removal of supernatant liquid may be performed by suction of through conduit 36 in lowered position after the centrifugation has been terminated, the precipitate being sedimented on the cylindrical walls 20. After a centrifugation and removal of supernatant liquid, the sedimented precipitate may be scraped from the walls by slowly rotating the centrifuge vessel 18, the scraper 40 being kept in the position shown by the full lines. Mixing and dissolution operations may be easily performed in the apparatus 10. Liquids may be added to the centrifuge vessel through the conduit 36, and solids may be added e.g. through the tube 32. The necessary agitation may be performed either by rotating the centrifuge vessel 32 at a suitable speed while keeping the stirrer 40 in a fixed position, or by rotating the stirrer 40 in the stationary centrifuge vessel, or by combining both types of rotation. Evaporation from the centrifuge vessel 16 may be performed by connecting the tube 32 to a vacuum source by means of the joint 34. The heat necessary for the evaporation or distillation is applied by means of the heating coils 24, and if desired, agitation may be performed during evaporation or distillation, either by rotating the centrifuge vessel (provided that the sealing means 30 is of a type which permits rotation while closing vacuum-tightly) or by rotating the stirrer 40, or by a combination of both types of rotation. If desired, an inert gas can be introduced through the line 36 during distillation. Drying is most conveniently performed in the apparatus 10 by applying heat by means of the heating coils, possibly applying vacuum and preferably agitating by means of one or both types of rotation discussed above, and it is also possible and often preferable to use a drying gas introduced through conduit 36.

As will be understood from the above explanation, the application of a centrifuge vessel as reaction vessel for peptide syntheses according to the in situ principle offers several advantages, and especially the combination of the possibility of centrifugation with the possibility of evaporation from the same vessel, as well as mixing within the same vessel, secures efficient unit operations which may easily be automated. Evidently, several modifications of the apparatus set out in principle above may be made, including the replacement of the single conduit 36 with several conduits (one for gas introduction, one for addition of acid, one for addition of solvent or nonsolvent, one for removal of liquid from the vessel, etc.) The structural materials or inner coatings used in the apparatus 10 should be so chosen that the apparatus surfaces which are to contact reactants, reaction mixtures, byproducts, etc. are resistant thereto. Thus, for example, the said surfaces should be resistant to moderately strong acids such as trifluoroacetic acid or hydrochloric acid in acetic acid, and they should be able to resist solvents such as dimethylformamide, dimethylsulfoxide, ether, ethylacetate, ethanol, and bases such as triethylamine, diisopropylamine, or N-methylmorpholine. Silver, teflon, polypropylene, glass and several other materials are known which will fulfil the above conditions.

EXAMPLE tert.Butyloxycarbonyl-L-leucyl-L-leucyl-L-glutaminylglycyl-L-leucyl-L-valinamide (I).

The protected pentapeptide amide, tert,butyloxcarbonyl-L-leucvl-L-glutaminylglycyl-L-leucyl-L-valinamide (5.81 g, 9.26 mmol), is dissolved in trifluoroacetic acid (15 ml). After about 15 min. at room temperature, the trifluoroacetic acid is removed in vacuo and the residue treated with ether (50 ml). The precipitated trifluoroacetate salt is washed with ether (50 ml), dried in vacuo and dissolved in dimethylformamide (60 ml). Triethylamine (2.8 ml) and tert.butyloxycarbonyl-L-leucine ortho-nitrophenyl ester (4.89 g, 13.9 mmol, 50% excess) are added with thorough mixing. From time to time, small samples are withdrawn, spotted on filter paper and tested with ninhydrin. After the complete disappearance of the amino-component, most of the solvent is removed in vacuo and ethyl acetate (50 ml) is added to the residue. The precipitate is separated from the solution and is washed with ethyl acetate (100 ml). After drying in vacuo, the product, the desired hexapeptide I, weighs 6.75 g (98.4%), sinters at 255° and melts with decomposition at 263° – 265°; $[\alpha]_D^{25}$ – 47.8° (c 2, AcOH). It gives a single spot ($R_f$ 0.75) on thin layers of silica gel in the solvent system n-butanol - acetic acid - water (4:1:1). A hydrolysate gives the following amino acid analysis: Glu, 1.0; Gly, 1.0; Val, 1.0; Leu, 3.1.

Analysis:
Calculated for $C_{35}H_{64}N_8O_9$: C, 56.74; H, 8.71; N, 15.1.
Found: C, 56.58; H, 8.61; N, 14.9.

The above deprotection step and all subsequent operations may (in smaller scale) be carried out in a centrifuge tube prepared from a 28 mm OD glass tube ending in a 24/40 standard tapered glass joint. The vessel formed in this way (ca. 40 ml) is provided with a drying tube containing cotton during the deprotection and with a 24/40 ground glass stopper during coupling reactions. A simple bench instrument (International Clinical Centrifuge, Model CL) may be used for the separation of solids from the supernatant solutions. For evaporation of solvents, the tube may be attached to all glass rotary evaporators. The product may be dried and weighed in the same tube.

All the operations described below were carried out in the above-mentioned equipment; the intermediates were not removed from the vessel at any time during the chain-lengthening steps. Trifluoroacetic acid was used for the (partial) deprotection of the peptides and triethylamine for the liberation of the amines from their trifluoroacetate salts. Stepwise acylation was accomplished with a gradual increase from 20% to 50% excess of the respective protected amino acid o-nitrophenyl esters, except in the preparation of the tetrapeptide where, to suppress pyroglutamyl peptide formation, a 100% excess was applied:

A sample of t.butyloxycarbonyl-L-valinamide (400 mg, 1.85 mmol) was placed in the centrifuge tube and dissolved in trifluoroacetic acid (1 ml). After 15 min. at room temperature, the excess trifluoroacetic acid was removed in vacuo. The trifluoroacetate salt was triturated with ether, the solution removed after centrifugation, the solid washed with ether (45 ml in 3 portions) and dried in vacuo to give the amide trifluoroacetate (416 mg, 98%). The amide trifluoroacetate was dissolved in dimethylformamide (2 ml), triethylamine (270 λ) was added followed by tert.butyloxycarbonyl-L-leucineortho-nitrophenyl ester (763 mg, 2.2 mmol). After 24 hr the dimethylformamide was removed in vacuo at 35°. The residue was triturated and washed with ethyl acetate (15 ml in 5 portions). The dry product (tert.butyloxycarbonyl-L-leucyl-valinamide) weighed 534 mg (90%) (No attempt was made to secure additional material from the mother Liquors and washings.). Melting points and $R_f$ values were similar to authentic samples.

Following this procedure, stepwise chain-lengthening was performed to build up the hexapeptide I in this small scale apparatus.

I claim

1. In a process for the synthesis of peptides by the reaction of a peptide or amino acid having a free amino group with a coupling peptide or amino acid having a protected amino group and an activated carboxyl group, wherein additional functional groups are protected, the improvement comprising conducting said synthesis in a single reactor vessel comprising the steps of charging to said vessel a non-polymerbound peptide or amino acid protected on its free amino group by a removable protecting group, adding sufficient acid to acidolytically remove the amino-protecting group from the peptide or amino acid and form a salt of said peptide or amino acid, adding to said vessel an organic solvent precipitant to form a solid precipitated peptide or amino acid salt and a liquid phase, separating the solid and removing the liquid phase from the vessel while retaining the solid peptide or amino acid in said vessel; dissolving or suspending said solid peptide or amino acid in a solvent suitable for an acylation reaction by adding the solvent to said vessel; acylating the free amino group of said peptide or amino acid by adding an organic base and an acylating peptide or amino acid having an N-protected amino group and an activated carboxyl group whereby said activated carboxyl group of the acylating peptide or amino acid reacts with the free amino group of the peptide or amino acid to couple said peptides or amino acids in said vessel; adding a non-solvent for the resulting coupled peptide to said vessel to precipitate the coupled peptide, and separating and removing the liquid phase from the vessel to provide the isolated solid peptide product, wherein all intermediates formed during said reactions are isolated in said reactor vessel.

2. A method according to claim 1 wherein the steps are repeated one or more times to couple one or more additional peptides or amino acids thereby lengthening the peptide chain.

3. A method according to claim 1 wherein the non-polymer bound peptide or amino acid is a peptide.

4. A method according to claim 1 wherein the non-polymer peptide or amino acid is an amino acid.

5. A process as claimed in claim 1 wherein separation of liquid phases from solid phases is performed by centrifugation of the mixture in the vessel and removal of liquid from the vessel.

6. A process as claimed in claim 1 wherein separation of the liquid phases from solid phases is performed by filtration with removal of the filtrate from the vessel.

7. A process as claimed in claim 1 wherein the acid used in the acidolytical removal of the amino-protecting group from the peptide is trifluoroacetic acid.

8. A process as claimed in claim 1 wherein the acid used in the acidolytical removal of the amino-protecting group from the peptide is HCl in acetic acid or HBr in acetic acid.

9. A process as claimed in claim 1 wherein after acidolytically removing the amino-protecting group, the solution is removed from the vessel by evaporation in vacuo to provide a residue of a peptide salt or amino acid salt.

10. A process as claimed in claim 9 wherein the residue is subsequently dried by contact with a stream of an inert gas introduced into the vessel.

11. A process as claimed in claim 9 wherein the organic solvent precipitant of the peptide salt is a dialkyl ether.

12. A process as claimed in claim 11 wherein the dialkyl ether is diethyl ether.

13. A process as claimed in claim 1 wherein the organic solvent used in the acylating step is dimethylformamide or dimethylsulfoxide.

14. A process according to claim 13 wherein the base used in a tertiary or quaternary base.

15. A process as claimed in claim 14 wherein the base is selected from the group consisting of triethylamine, diisopropylethyl amine, and N-methylmorpholine.

16. A process as claimed in claim 14 wherein the N-protected amino acid in activated form is an activated ester of an N-protectd amino acid.

17. A process as claimed in claim 16 wherein the activated ester is a p-nitrophenyl or o-nitrophenyl ester.

18. A process as claimed in claim 16 wherein the nonsolvent used is a liquid in which the protected peptide derivative is substantially insoluble, and in which excess active acylating acid derivative and the by-products present are substantially soluble.

19. A process as claimed in claim 18 wherein the nonsolvent is ethyl acetate.

20. A process as claimed in claim 18 wherein the nonsolvent is chloroform.

* * * * *